United States Patent
Yamane (10) Patent No.: US 12,376,933 B2
(45) Date of Patent: Aug. 5, 2025

(54) MICROSCOPE DRAPE

(71) Applicant: MEILLEUR CO., LTD., Funabashi (JP)

(72) Inventor: Tsurashi Yamane, Funabashi (JP)

(73) Assignee: MEILLEUR CO., LTD, Funabashi (JP)

( * ) Notice: Subject to any disclaimer, the term of this patent is extended or adjusted under 35 U.S.C. 154(b) by 0 days.

(21) Appl. No.: 18/867,621

(22) PCT Filed: Nov. 10, 2023

(86) PCT No.: PCT/JP2023/040597
§ 371 (c)(1),
(2) Date: Nov. 20, 2024

(87) PCT Pub. No.: WO2025/099931
PCT Pub. Date: May 15, 2025

(65) Prior Publication Data
US 2025/0152288 A1   May 15, 2025

(51) Int. Cl.
*A61B 46/10* (2016.01)
*A61B 90/20* (2016.01)
*G02B 27/00* (2006.01)

(52) U.S. Cl.
CPC .............. *A61B 46/10* (2016.02); *A61B 90/20* (2016.02); *G02B 27/0006* (2013.01)

(58) Field of Classification Search
CPC ......... A61B 46/10; A61B 90/20; A61B 90/50; A61B 90/25; A61B 3/13; A61B 3/132;
(Continued)

(56) References Cited

U.S. PATENT DOCUMENTS

| 5,608,574 A | 3/1997 | Heinrich |
| 2005/0286130 A1 | 12/2005 | Bala |

(Continued)

FOREIGN PATENT DOCUMENTS

| CN | 102711652 A | 10/2012 |
| JP | 2002-072038 A | 3/2002 |

(Continued)

OTHER PUBLICATIONS

Dec. 12, 2023 International Search Report issued in International Patent Application No. PCT/JP2023/040597.
(Continued)

*Primary Examiner* — Jie Lei
(74) *Attorney, Agent, or Firm* — Oliff PLC (57) ABSTRACT

A microscope drape capable of further facilitating an operation of attachment is provided. A microscope drape includes a lens cap unit; a protective lens; and a drape main body. The lens cap unit includes: a cylindrical body having; a plurality of protrusions provided at positions spaced apart from each other in a circumferential direction of the cylindrical body to protrude inwardly in a radial direction from an inner curved surface of the cylindrical body, respectively; and a biasing member for biasing at least one of the plurality of protrusions in a direction of protruding from the inner curved surface of the cylindrical body, the at least one of the plurality of protrusions being supported to be retractable in the cylindrical body. The protective lens is supported at a distal end of the cylindrical body with being tilted with respect to an optical axis of the objective lens.

7 Claims, 10 Drawing Sheets

(58) Field of Classification Search
CPC . A61B 1/045; A61B 1/00149; A61B 1/00142; G02B 21/00; G02B 27/00; G02B 21/0012; G02B 21/22; G02B 21/18; G02B 21/24; G02B 21/082; G02B 27/0006
USPC ......... 359/510, 507, 508, 511–514; 600/249, 600/122, 133, 109, 131
See application file for complete search history.

(56) References Cited

U.S. PATENT DOCUMENTS

| | | |
|---|---|---|
| 2008/0144178 A1 | 6/2008 | Dillon et al. |
| 2011/0155145 A1 | 6/2011 | Chua |
| 2014/0240832 A1 | 8/2014 | Nakamura et al. |
| 2017/0168292 A1 | 6/2017 | Koenig et al. |
| 2021/0405353 A1 | 12/2021 | Yamane et al. |

FOREIGN PATENT DOCUMENTS

| | | |
|---|---|---|
| JP | 2010-512851 A | 4/2010 |
| JP | 2012-183449 A | 9/2012 |
| JP | 2014-161504 A | 9/2014 |
| JP | 2017-107210 A | 6/2017 |
| KR | 10-2192279 B1 | 12/2020 |
| WO | 2022/003806 A1 | 1/2022 |

OTHER PUBLICATIONS

Dec. 12, 2023 Written Opinion issued in International Patent Application No. PCT/JP2023/040597.
Nov. 30, 2023 Office Action issued in Japanese Patent Application No. 2023-570453.

MICROSCOPE DRAPE

TECHNICAL FIELD

The present invention relates to a microscope drape for covering a surgical microscope.

BACKGROUND ART

In the neurosurgery, otorhinolaryngology, orthopedics, and ophthalmology, there are cases that surgery is performed using a surgical microscope to enlarge a surgical field. Surgery has to be performed in under sterile conditions, however, since it is difficult to sterilize the surgical microscope per se, in common cases, the surgical microscope is covered with a disposable microscope drape to secure sterile conditions in each surgery (see, for example, Patent Literatures 1 to 4).

A typical microscope drape includes a lens cap to be attached to and detached from an objective lens of a surgical microscope, and a bag-shaped drape main body to be attached to a lens cap unit to cover the surgical microscope. Furthermore, Patent Literature 5 discloses various examples of a lens cap unit capable of being attached to objective lens having the diameter size different from each other, and also discloses a technique of changing the angle of a protective lens relative to an optical axis to prevent reflection and glare of an incident light in a surgical microscope.

CITATION LIST

Patent Literature

Patent Literature 1: JP-A-2012-183449
Patent Literature 2: JP-A-2014-161504
Patent Literature 3: JP-A-2010-512851
Patent Literature 4: JP-A-2017-107210
Patent Literature 5: WO2022/003806

SUMMARY OF INVENTION

Technical Problem

However, the microscope drape according to Patent Literature 5 causes a problem that an operation of attaching the lens cap unit to the objective lens is complicated (for example, it greatly differs from a procedure of attaching the microscope drape as commonly performed, it requires a large force in an operation of attachment, etc.).

The present invention has been made in view of the problems above in the prior art, and an object of the present invention is to provide a microscope drape capable of further facilitating an operation of attachment thereof to a surgical microscope.

Solution to Problem

In order to solve the problems described above, the present invention provides a microscope drape comprising: a lens cap unit to be attached to and detached from a housing of an objective lens of a surgical microscope; a protective lens for protecting the objective lens; and a drape main body for covering the surgical microscope, wherein the lens cap unit includes: a cylindrical body having an inner diameter being more than that of the housing; a plurality of protrusions provided at positions spaced apart from each other in a circumferential direction of the cylindrical body to protrude inwardly in a radial direction from an inner curved surface of the cylindrical body, respectively; and a biasing member for biasing at least one of the plurality of protrusions in a direction of protruding from the inner curved surface of the cylindrical body, the one of the plurality of protrusions being supported to be retractable in the cylindrical body, and the protective lens is supported at a distal end of the cylindrical body with being tilted with respect to an optical axis of the objective lens.

Advantageous Effects of Invention

According to the present invention, it is possible to provide a microscope drape capable of further facilitating an operation of attachment thereof to a surgical microscope.

DESCRIPTION OF EMBODIMENTS

Hereinafter, a microscope drape 10 according to embodiments will be described with reference to the drawings. It should be noted that the embodiments of the present invention to be described below are examples for embodying the present invention, and the scope of the present invention is not limited to the scope described in the embodiments. Therefore, the present invention can be realized as well if various modifications are made to the embodiment.

Figure 1:
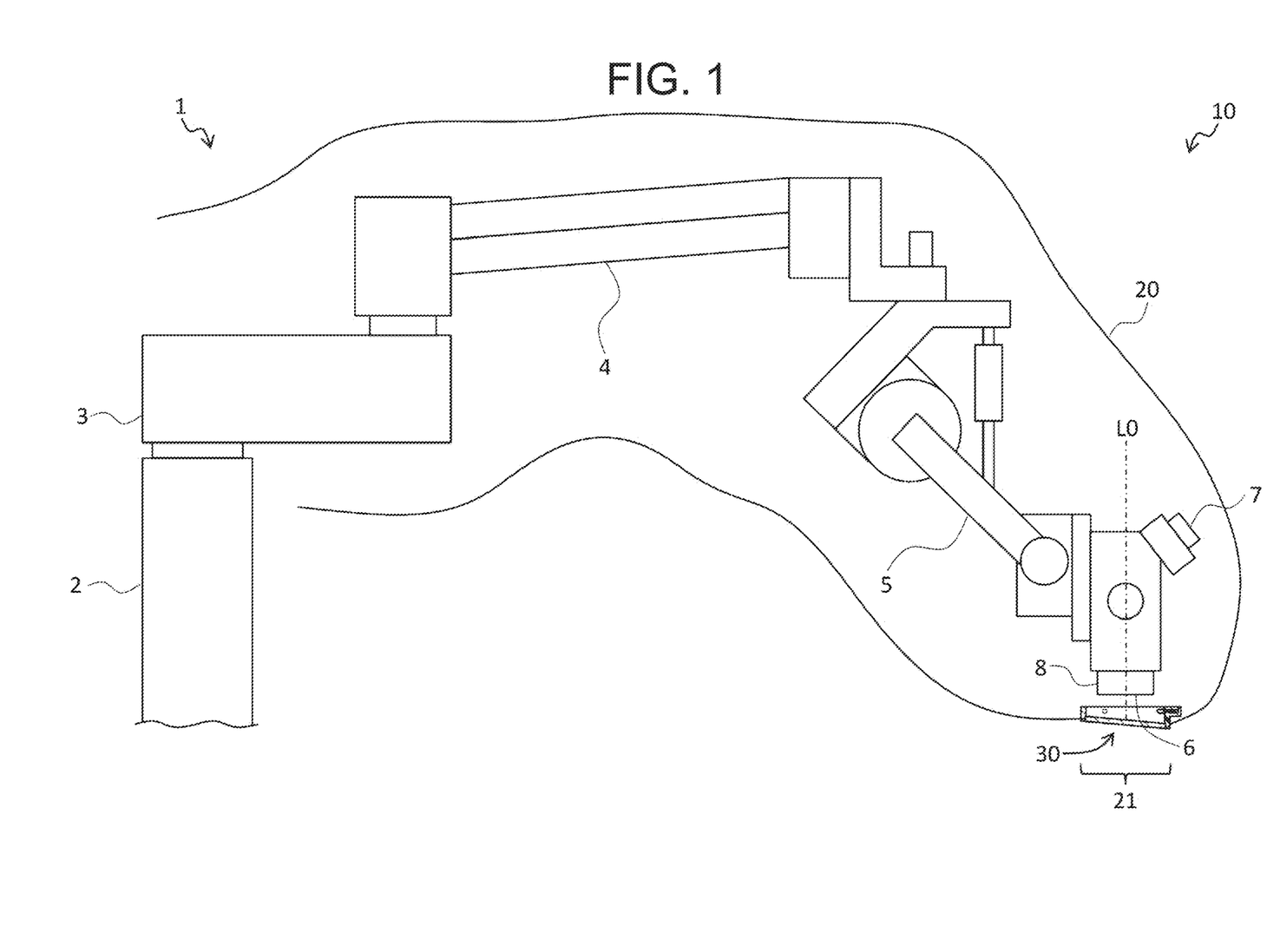
FIG. 1 is a schematic diagram of a main part of a surgical microscope and a microscope drape.

FIG. 1 is a schematic diagram of a main part of a surgical microscope 1 and the microscope drape 10. As illustrated in FIG. 1, the surgical microscope 1 mainly includes a plurality of arms 2, 3, 4, 5 rotatably connected to each other, an objective lens 6 attached to the distal end of the arm 5, and an eyepiece lens 7. Rotation of the joint portions of the arms 2 to 5 relative to each other causes the objective lens 6 to be placed at a position facing the surgical field. In this state, a physician (surgeon) looks through the eyepiece 7, whereby he or she can observe the enlarged surgical field.

The objective lens 6 is a convex lens. The objective lens 6 is attached to the inside of a cylindrical housing 8. That is, an optical axis L0 of the objective 6 illustrated with a dashed-and-dotted line in FIG. 1 matches the axial direction of the housing 8.

The surgical microscope 1 further includes an illumination device (for example, an LED or a xenon lamp). A light emitted from the illumination device passes through the objective lens 6 via an optical system (a lens, a mirror, etc.) housed in the arms 2 to 5, and is irradiated toward the surgical field. This light is reflected by the surgical field and enters the objective lens 6 again, whereby the physician can observe the surgical field. An irradiation direction of the light by the illumination device is tilted by, for example, about 3° to 6° relative to the optical axis L0.

All equipment that touches or possibly touches the surgical field during the surgery has to be sterilized. However, it is difficult to sterilize the surgical microscope 1 per se, and thus the surgical microscope 1 is covered with the disposable microscope drape 10 in each operation. The microscope drape 10 is packaged with being sterilized, and an operator unpacks the microscope drape 10 in an operating room and then covers it on the surgical microscope 1.

First Embodiment

As illustrated in FIG. 1, the microscope drape 10 according to the first embodiment mainly includes a drape main body 20 and a lens cap unit 30.

The drape main body 20 is a sheet-shaped member made of a transparent or semi-transparent material (for example, polyethylene). The drape main body 20 may have any known shape as long as it can cover the main part of the surgical microscope 1. For example, the drape main body 20 may have a simple sheet or bag shape. For another example, the drape main body 20 may include a first drape and a second drape each having a long strip shape, as disclosed in JP-B-6749532. For yet another example, the drape main body 20 may include a bag-shaped portion and a band-shaped portion, as disclosed in JP-B-7122054.

The lens cap unit 30 is attached to the drape main body 20. More specifically, the lens cap unit 30 is welded to an outer edge portion of a through hole 21 penetrating the drape main body 20 in the thickness direction, which brings the microscope drape 10 to be integrated with the lens cap unit 30. The lens cap unit 30 is further attached to the housing 8. The lens cap unit 30 suppresses the reflection and glare of an incident light in the surgical microscope 1.

[Structure of Lens Cap Unit 30]

Figure 2A:
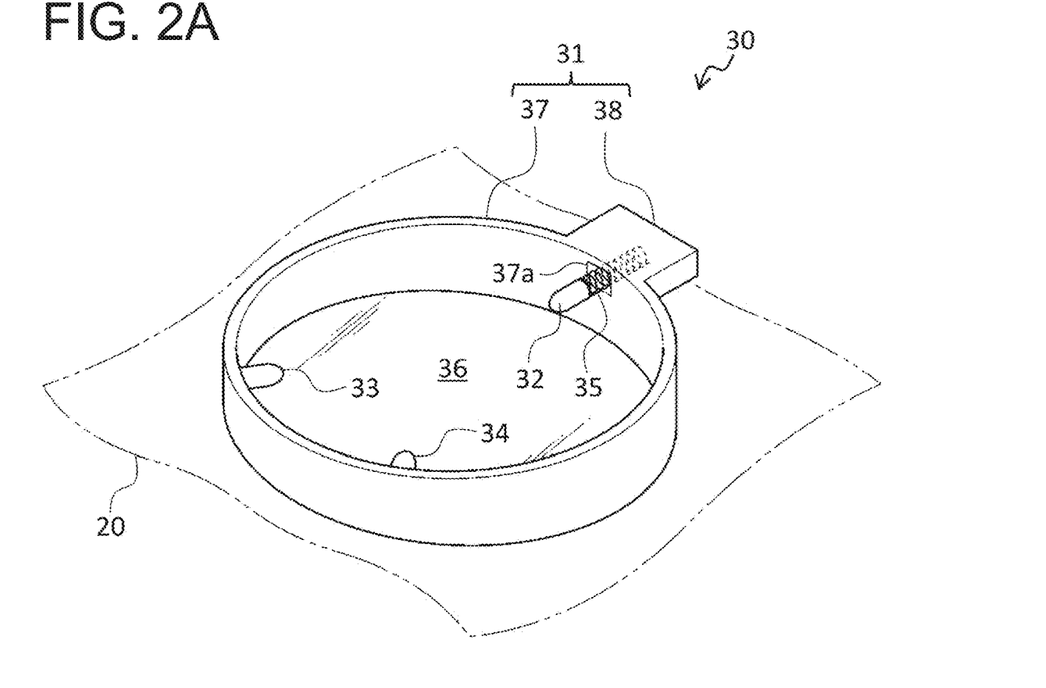
FIG. 2A is a perspective view of a microscope drape according to the first embodiment as viewed obliquely from above.
Figure 2B:
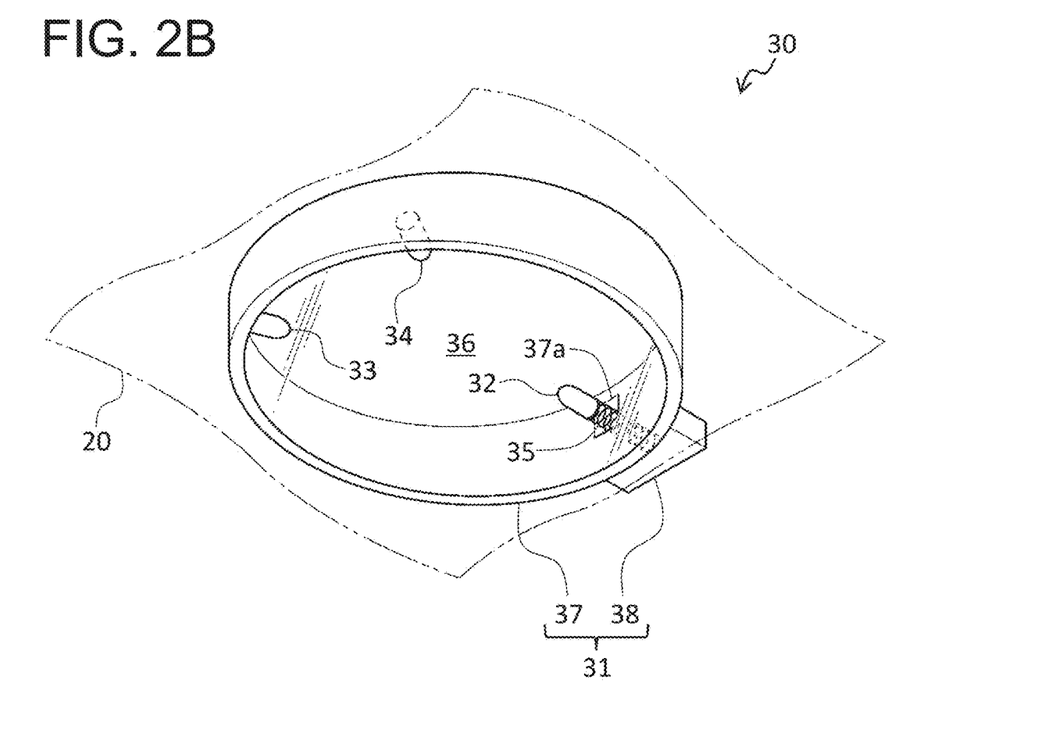
FIG. 2B is a perspective view of a microscope drape according to the first embodiment as viewed obliquely from below.
Figure 3A:
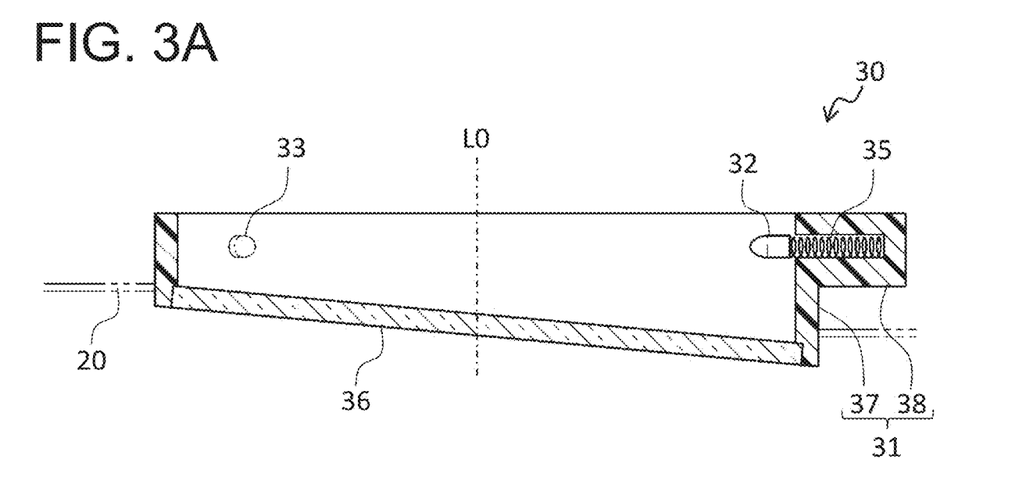
FIG. 3A is a longitudinal section view of a microscope drape according to the first embodiment.
Figure 3B:
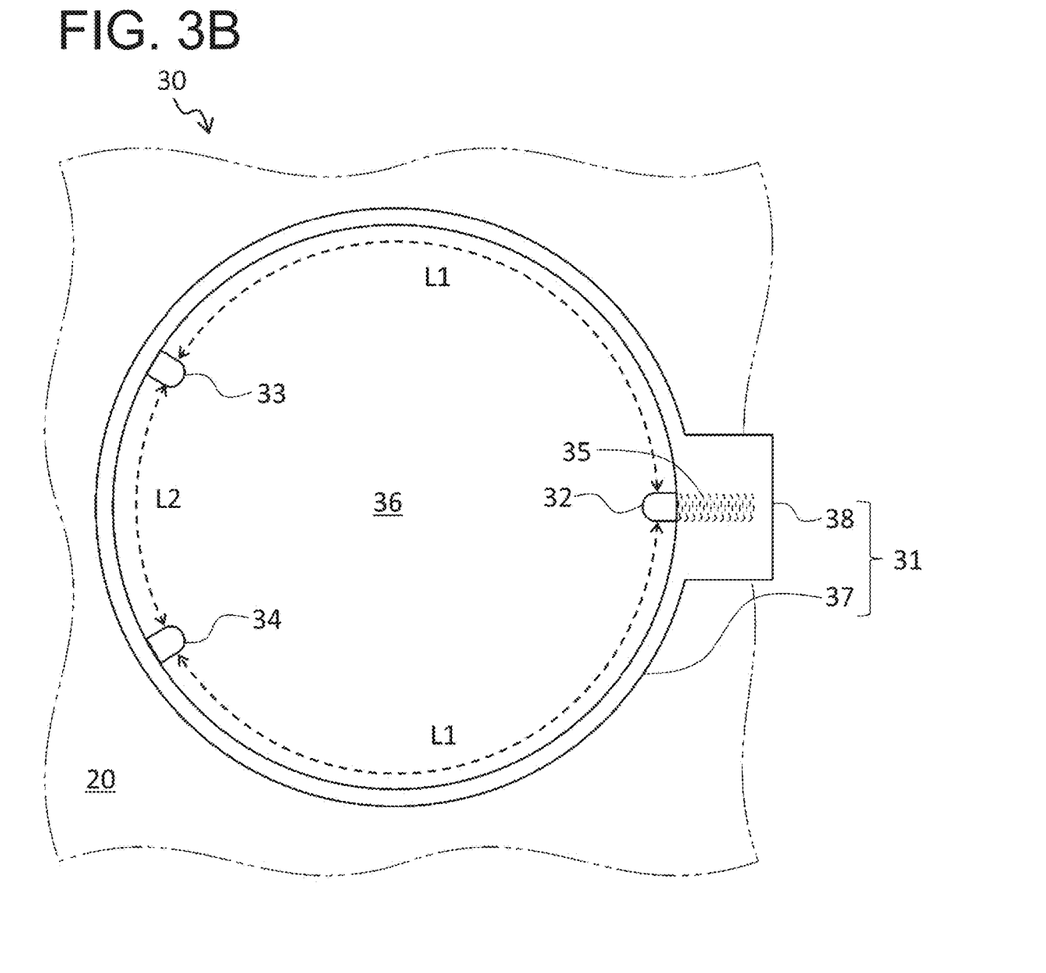
FIG. 3B is a top view of a microscope drape according to the first embodiment.

FIG. 2A is a perspective view of the microscope drape 10 according to the first embodiment as viewed obliquely from above. FIG. 2B is a perspective view of the microscope drape 10 according to the first embodiment as viewed obliquely from below. FIG. 3A is a longitudinal section view of the microscope drape 10 according to the first embodiment. FIG. 3B is a top view of the microscope drape 10 according to the first embodiment.

As illustrated in FIG. 2A to FIG. 3B, the lens cap unit 30 mainly includes a cap main body 31, a plurality of protrusions 32, 33, 34 (three in the present embodiment), a coil spring 35 (an example of the biasing member), and a protective lens 36.

The cap body 31 is a member for supporting the protrusions 32 to 34, the coil spring 35, and the protective lens 36, and to be attached to the housing 8. The cap main body 31 is made of, for example, resin (for example, polypropylene). The cap main body 31 is formed with, for example, a combination of a cylindrical body 37 and a housing portion 38.

The cylindrical body 37 has a cylindrical shape with both the ends in the axial direction being opened. The inner diameter of the cylindrical body 37 is set to be more than the outer dimension of the housing 8 of various type to which the lens cap unit 30 is expected to be mounted. The outer curved surface of the cylindrical body 37 is welded to the outer edge portion of the through hole 21 of the drape main body 20. As illustrated in FIG. 3A, in the cylindrical body 37 according to the first embodiment, the length in the axial direction differs over the circumferential direction of the cylindrical body 37. More specifically, one end of the cylindrical body 37 in the axial direction (upper end in FIG. 3A) is perpendicular to the axial direction of the cylindrical body 37 illustrated with a dashed-and-dotted line in FIG. 3A. On the other hand, the other end of the cylindrical body 37 in the axial direction (lower end in FIG. 3A) is inclined relative to the axial direction of the cylindrical body 37.

The housing portion 38 is a portion projecting from the outer curved surface of the cylindrical body 37, at a portion of the circumferential direction of the cylindrical body 37. The housing portion 38 according to the first embodiment is formed at a portion of the cylindrical body 37 with the length in the axial length being the most within the circumferential direction of the cylindrical body 37. The housing portion 38 includes an internal space for housing the coil spring 35 therein. The cylindrical body 37 further includes a through hole 37a that penetrates the cylindrical body 37 in the thickness direction. The internal space of the cylindrical member 37 and the internal space of the housing portion 38 are communicated with each other via the through hole 37a.

The protrusions 32 to 34 are made of, for example, resin (for example, polyurethane). The protrusions 32 to 34 are arranged at positions spaced apart from each other in the circumferential direction of the cylindrical body 37. The protrusions 32 to 34 protrude inwardly in the radial direction from the inner curved surface of the cylindrical body 37. Among the protrusions 32 to 34, the protrusion 32 is a "movable protrusion 32", and the remaining two protrusions 33, 34 are "fixed protrusions 33, 34". It is noted that the number of protrusions 32 to 34 is not limited to three as long as it is two or more. It is also noted that the number of movable protrusions 32 is not limited to one as long as it is one or more. That is, all the protrusions 32 to 34 may be movable protrusions 32 to 34.

The movable protrusion 32 is placed at a position of the through hole 37a. The movable protrusion 32 is supported so as to be retractable (protrude and recede) into the cylindrical body 37. Here, the state that "the movable protrusion 32 is receded in the cylindrical body 37" does not necessarily have to be the state that the tip of movable protrusion 32 is completely receded in the cylindrical body 37, but may be the state that the amount of protrusion reduces more than that in the case where the movable protrusion 32 protrudes the most from the cylindrical body 37. Furthermore, the movable protrusion 32 is biased by the coil spring 35 in the direction of protruding from the inner curved surface of the cylindrical body 37. In the state where the movable protrusion 32 protrudes the most, the amounts of the protrusions 32 to 34 from the inner curved surface of the cylindrical body 37 may be the same to each other.

The fixed protrusions 33, 34 are fixed with protruding inwardly in the radial direction from the inner curved surface of the cylindrical body 37. In the circumferential direction of the cylindrical member 37, a distance L1 between the movable protrusion 32 and the fixed protrusion 33 is the same as a distance L1 between the movable protrusion 32 and the fixed protrusion 34. On the other hand, in the circumferential direction of the cylindrical member 37, a distance L2 between the fixed protrusions 33, 34 is less than the distances L1 between the movable protrusion 32 and the fixed protrusions 33, 34. However, the distances between the three protrusions 32 to 34 may be the same to each other (120° in the case of the first embodiment).

The protective lens 36 is a flat plate-shaped lens made of a material through which a light can transmit (for example, glass, polycarbonate, etc.). However, the protective lens 36 is not limited to the one having a flat plate shape, but may be a curved lens having a convex shape. The protective lens 36 is fixed to the end on the other side of the cylindrical body 37 in the axial direction (in the cylindrical body 37, the end on the side inclined relative to the axial direction). The protective lens 36 is supported at the distal end of the cylindrical member 37 with being inclined relative to the optical axis L0 of the objective lens 6. That is, one of both the ends of the cylindrical body 37 in the axial direction is opened while the other end is closed by the protective lens 36.

The protective lens 36 protects the objective lens 6 of the surgical microscope 1. More specifically, in the state where the lens cap unit 30 is attached to the housing 8, the protective lens 36 faces the objective lens 6 on the optical axis L0 of the objective lens 6. Then, an external light that has passed through the protective lens 36 enters the objective lens 6. The protective lens 36 is inclined relative to the optical axis L0, thereby suppressing the reflection and glare of the incident light in the surgical microscope 1.

[Attachment of Lens Cap Unit 30]

Figure 4A:
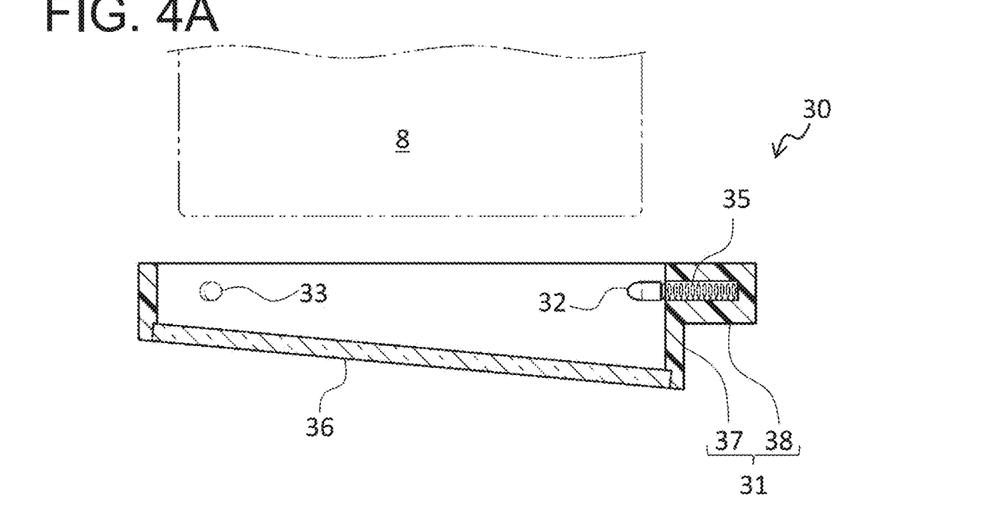
FIG. 4A is a longitudinal section view of a state before a lens cap unit according to the first embodiment is attached to a housing.
Figure 4B:
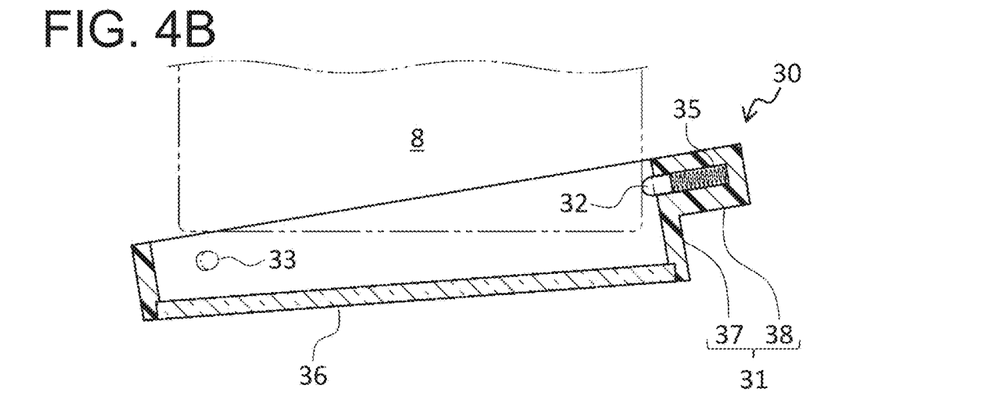
FIG. 4B is a longitudinal section view of a state while a lens cap unit according to the first embodiment is being attached to a housing.
Figure 4C:
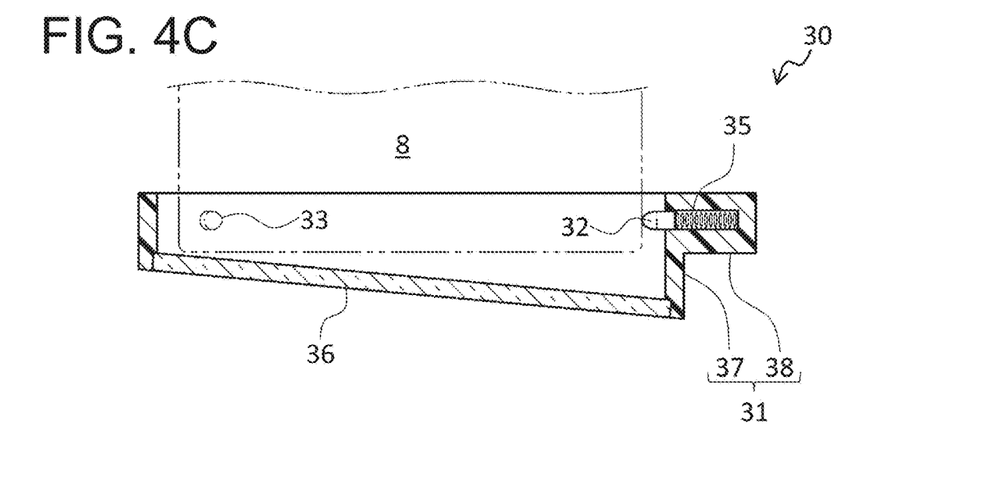
FIG. 4C is a longitudinal section view of a state after a lens cap unit according to the first embodiment is attached to a housing.
Figure 5A:
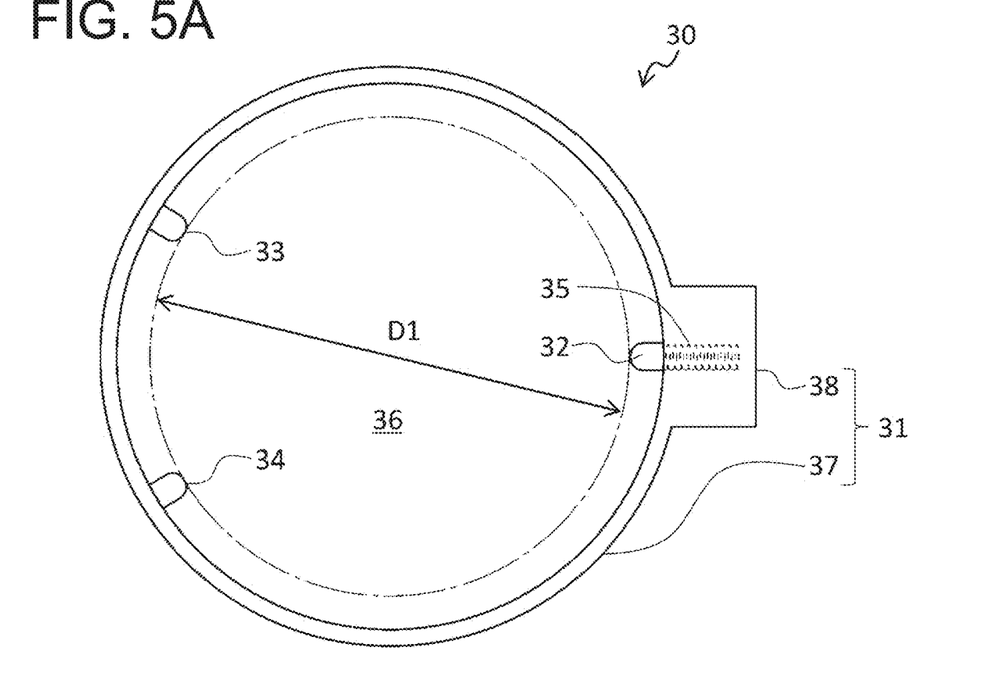
FIG. 5A is a top view of a state before a lens cap unit according to the first embodiment is attached to a housing.
Figure 5B:
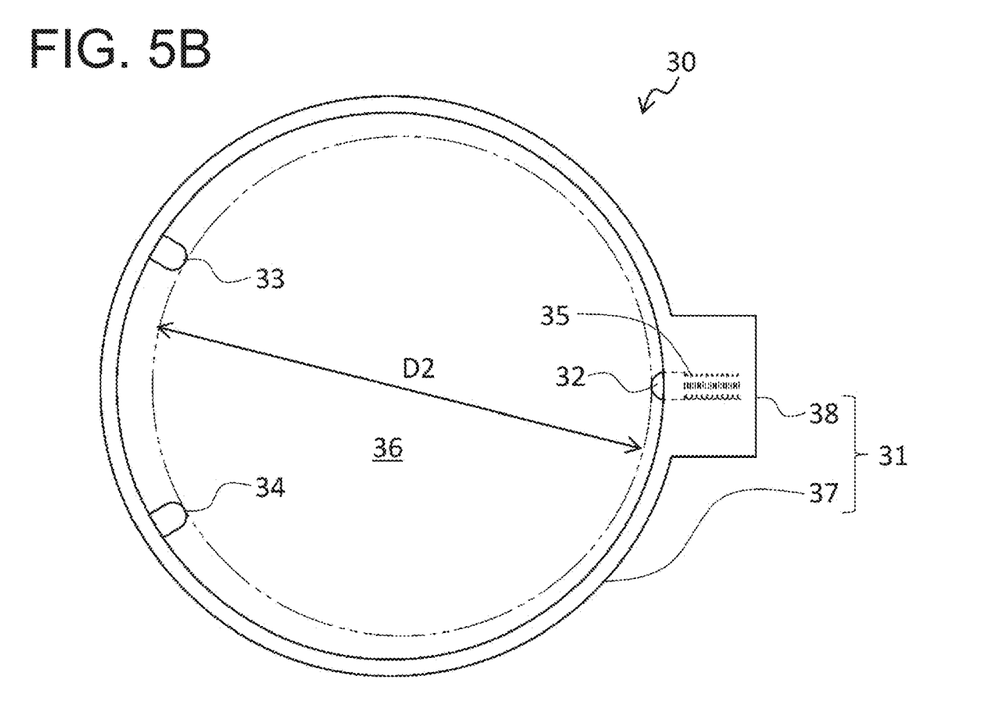
FIG. 5B is a top view of a state after a lens cap unit according to the first embodiment is attached to a housing.

FIG. 4 is a longitudinal section view of the states (A) to (C) illustrating before, during, after the attachment of the lens cap unit 30 according to the first embodiment to the housing 8, respectively. FIG. 5 is a top view of the states (A) and (B) before and after the attachment of the lens cap unit 30 according to the first embodiment to the housing 8, respectively.

Firstly, as illustrated in FIG. 4A, the lens cap unit 30 is placed below the housing 8 so that the open end of the cylindrical body 37 faces the lower surface of the housing 8 (that is, the open end of the cylindrical body 37 faces upward). In this state, as illustrated in FIG. 4A and FIG. 5A, the movable protrusion 32 is protruding the most.

Next, as illustrated in FIG. 4B, the cylindrical body 37 is made tilted so that the side on which the movable protrusion 32 is provided is positioned upwardly and the movable protrusion 32 is pressed against the side surface of the housing 8. This causes the movable protrusion 32 to be receded in the cylindrical body 37 against the biasing force of the coil spring 35 (in other words, reduce the amount of protrusion of the movable protrusion 32). On the other hand, in this state, the fixed protrusions 33, 34 are not in contact with the side surface of the housing 8.

Next, as illustrated in FIG. 4C, the cylindrical member 37 that has been tilted is brought back to its original state with the movable protrusion 32 being kept receded. This causes the cylindrical body 37 to be put around the housing 8. Then, the force in the direction of making the movable protrusion 32 receded is reduced to increase the amount of protrusion of the movable protrusion 32, so that the tips of the fixed protrusions 33, 34 come into contact with the side surface of the housing 8. Thus, the lens cap unit 30 is mounted to the housing 8. The amount of protrusion of the movable protrusion 32 in this state differs depending on the diameter of the housing 8.

Here, an imaginary circle connecting the tips of the protrusions 32 to 34 (dashed-and-dotted line in FIG. 5A) in the state where the movable protrusion 32 is protruding the most and an imaginary circle connecting the tips of the protrusions 32 to 34 (dashed-and-double-dotted line in FIG. 5B) in the state where the amount of protrusion of the movable protrusion 32 is reduced differ from each other by the amount of protrusion of the movable protrusion 32. Furthermore, a diameter D2 of the imaginary circle illustrated with the dashed-and-double-dotted line in FIG. 5B is more than a diameter D1 of the imaginary circle illustrated with the dashed-and-dotted line in FIG. 5A. That is, changing the amount of protrusion of the movable protrusion 32 causes the change in the diameter of the imaginary circle connecting the tips of the protrusions 32 to 34 (that is, diameter of the housing 8).

Next, the drape main body 20 is placed over surgical microscope 1 to be fixed thereto. Thus, the surgical microscope 1 can be maintained clean.

Operations and Effects According to First Embodiment

According to the first embodiment, as illustrated in FIG. 4A to FIG. 5B, the cylindrical body 37 is put around the housing 8 with the movable protrusion 32 being pressed against the side surface of the housing 8 and thus retracted into the cylindrical body 37, whereby the lens cap unit 30 can be attached to the housing 8. Thus, the operation of attaching the lens cap unit 30 to the surgical microscope 1 is simplified more than the cases of the various lens cap units exemplified in Patent Literature 5. Furthermore, contrary to the cases of the various lens cap units exemplified in Patent Literature 5, the lens cap unit 30 does not have to be elastically deformed greatly when being attached to the surgical microscope 1, which reduces the force required for the attachment.

Furthermore, according to the embodiment described above, placing the protrusions 32 to 34 at three positions enables the lens cap unit 30 to be attached to the housing 8 stably more than the case of placing the protrusions at two positions. In addition, providing the minimum number of three protrusions can make the structure of the lens cap unit 30 simple.

Still further, according to the embodiment described above, setting the distance L2 between the fixed protrusions 33, 34 less than the distances L1 between the movable protrusion 32 and the fixed protrusions 33, 34 enables the housing 8 to be stably held between the movable protrusion 32 and the fixed protrusions 33, 34.

Still further, attaching the protective lens 36 to the distal end of the cylindrical body 37 with being tilted relative to the optical axis L0 of the objective lens 6 enables prevention of the reflection and glare of an incident light in the surgical microscope 1. As a result, an operator can look through the surgical microscope 1 without being disturbed by the reflection and glare during the surgery.

Second Embodiment

Figure 6:
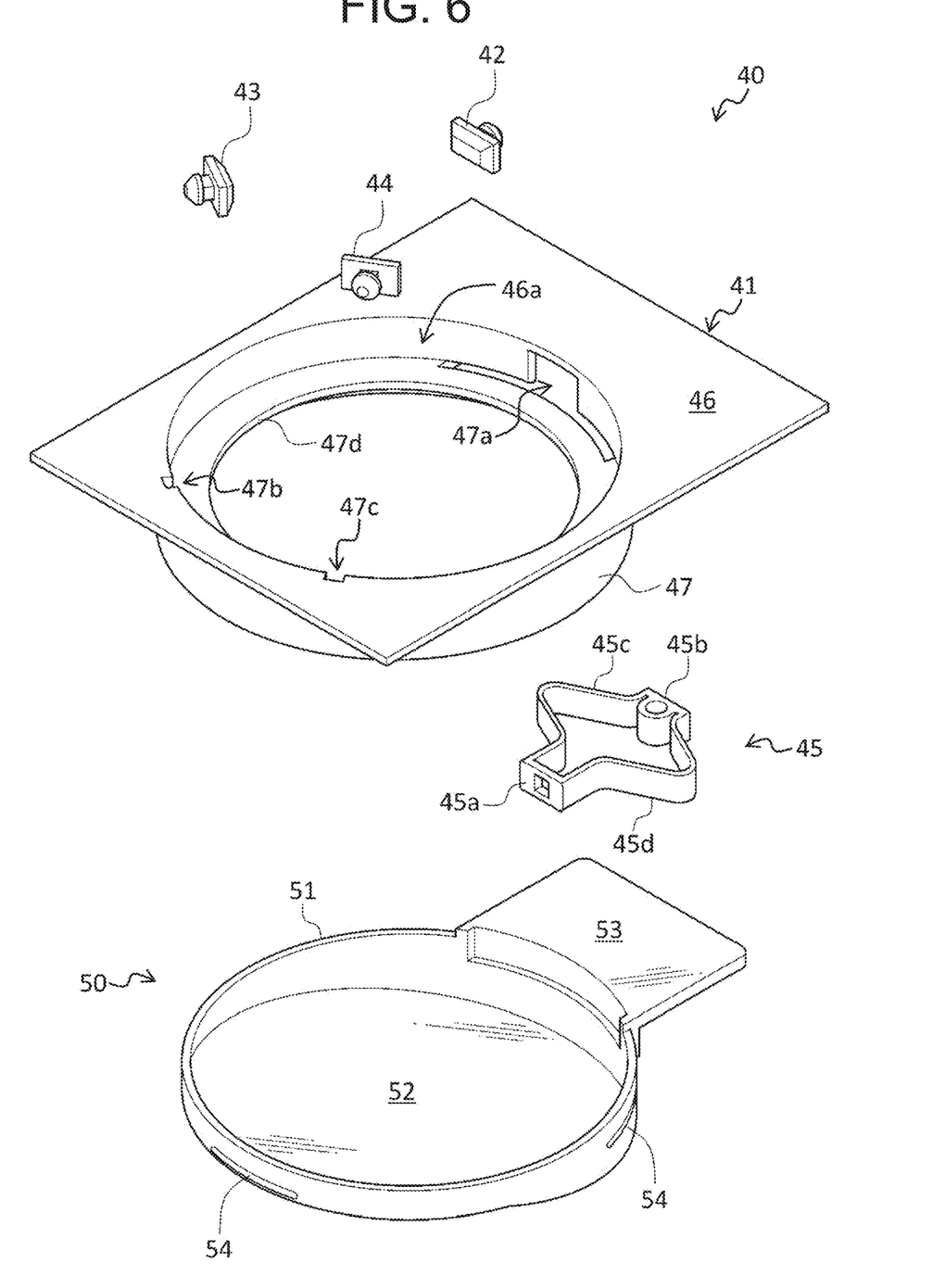
FIG. 6 is an exploded perspective view of a lens cap unit according to the second embodiment as viewed obliquely from above.
Figure 7:
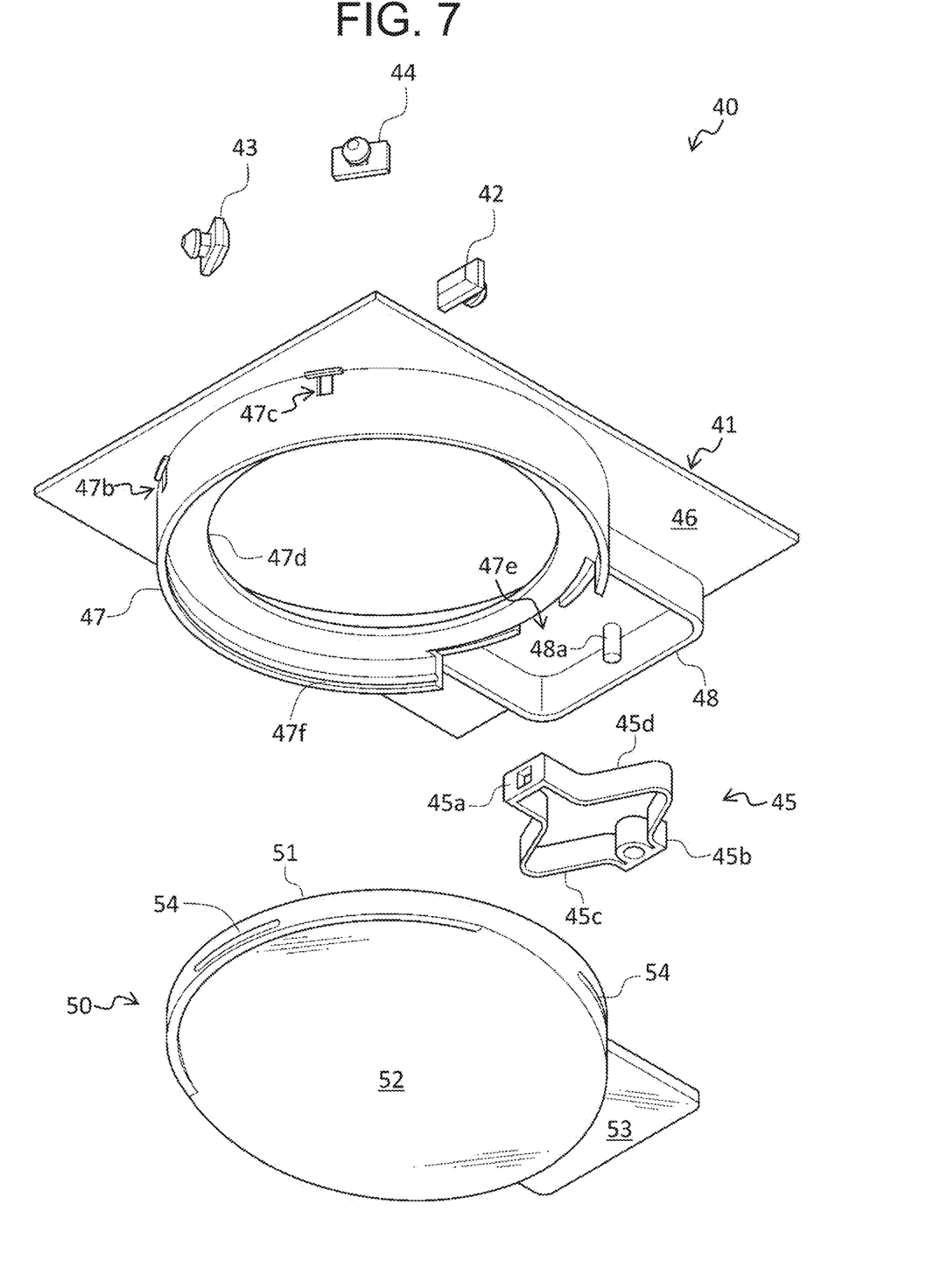
FIG. 7 is an exploded perspective view of a lens cap unit according to the second embodiment viewed obliquely from below.
Figure 8A:
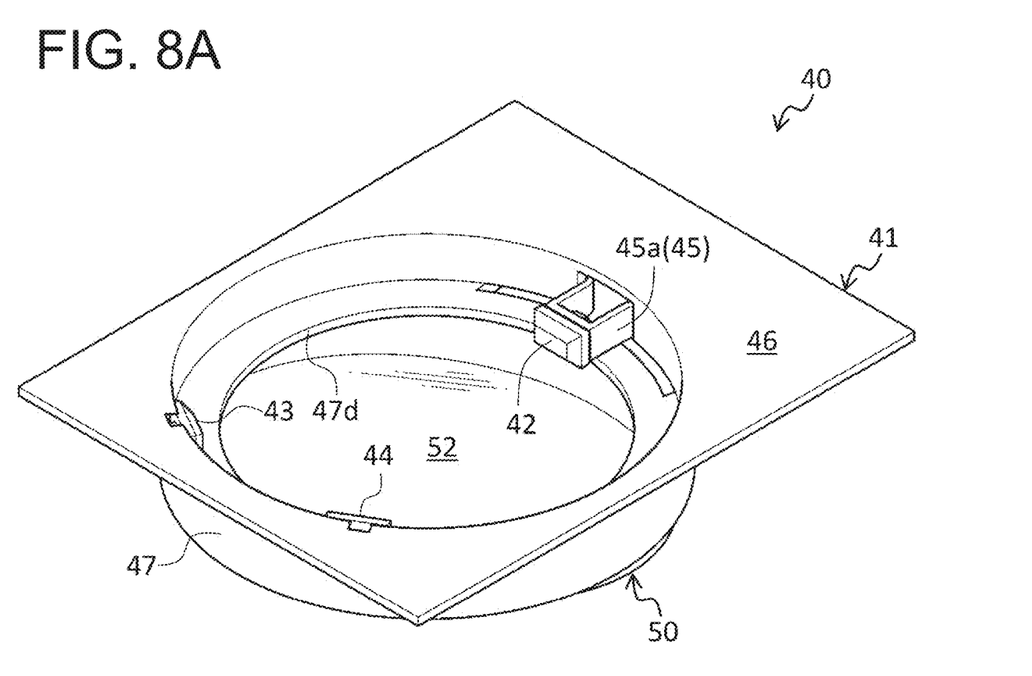
FIG. 8A is an assembled perspective view of a lens cap unit according to the second embodiment as viewed obliquely from above.
Figure 8B:
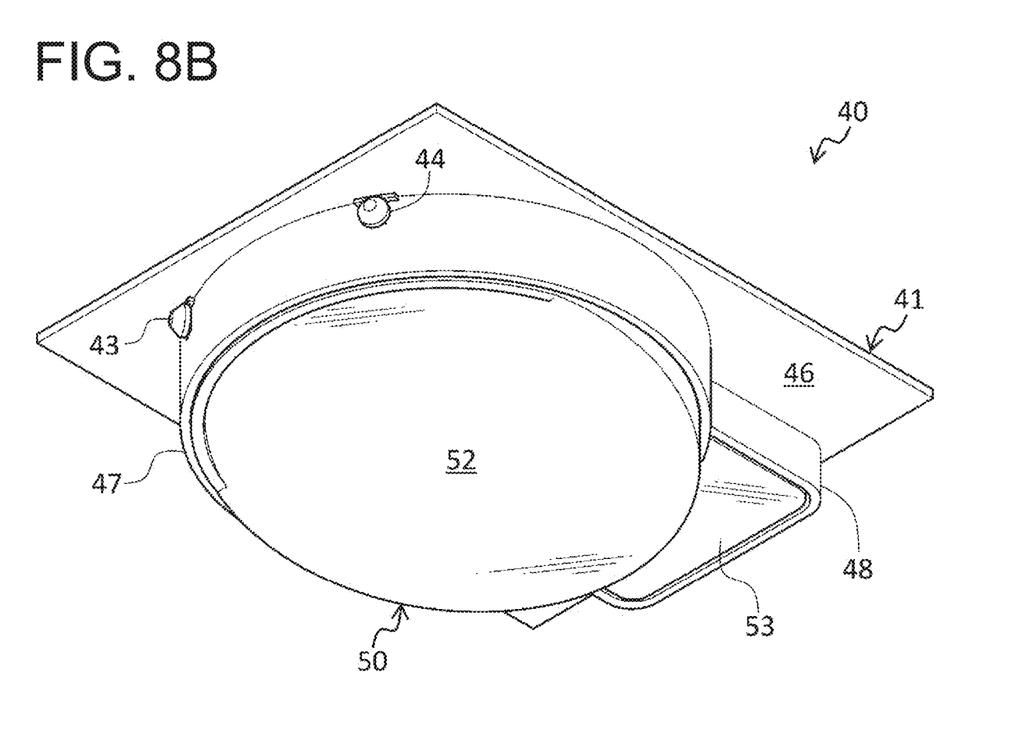
FIG. 8B is an assembled perspective view of a lens cap unit according to the second embodiment viewed obliquely from below.
Figure 9A:
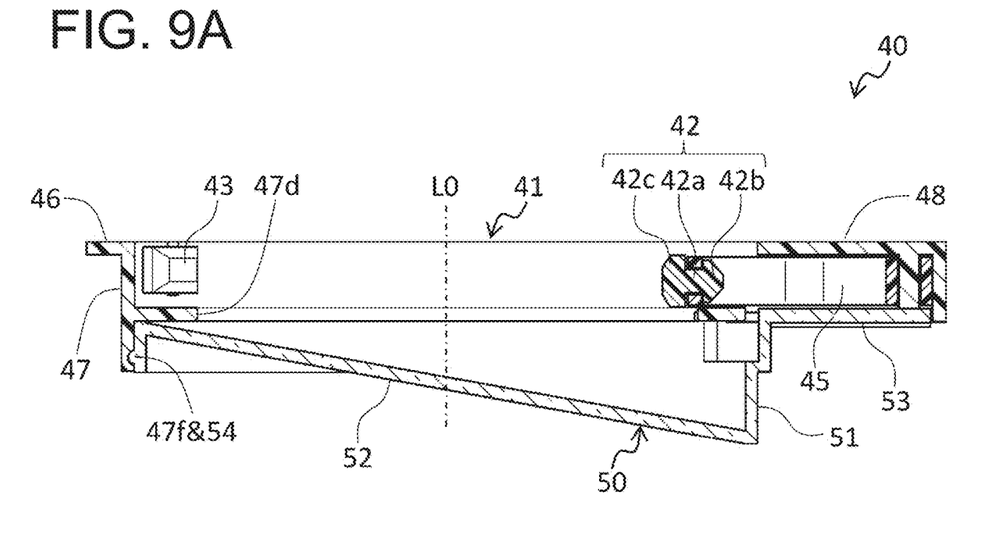
FIG. 9A is a longitudinal section view of a state before a lens cap unit according to the second embodiment is attached to a housing.
Figure 9B:
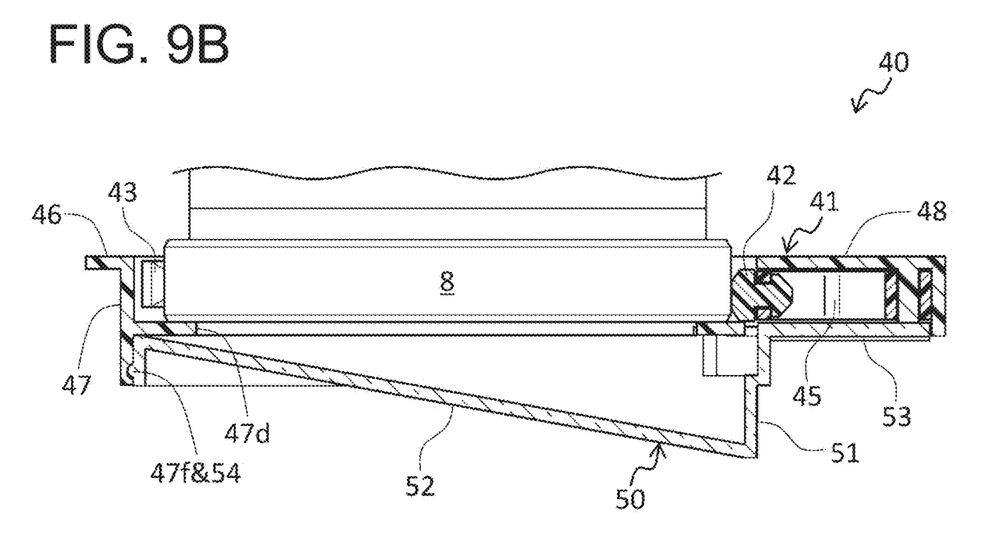
FIG. 9B is a longitudinal section view of a state after a lens cap unit according to the second embodiment is attached to a housing.
Figure 10A:
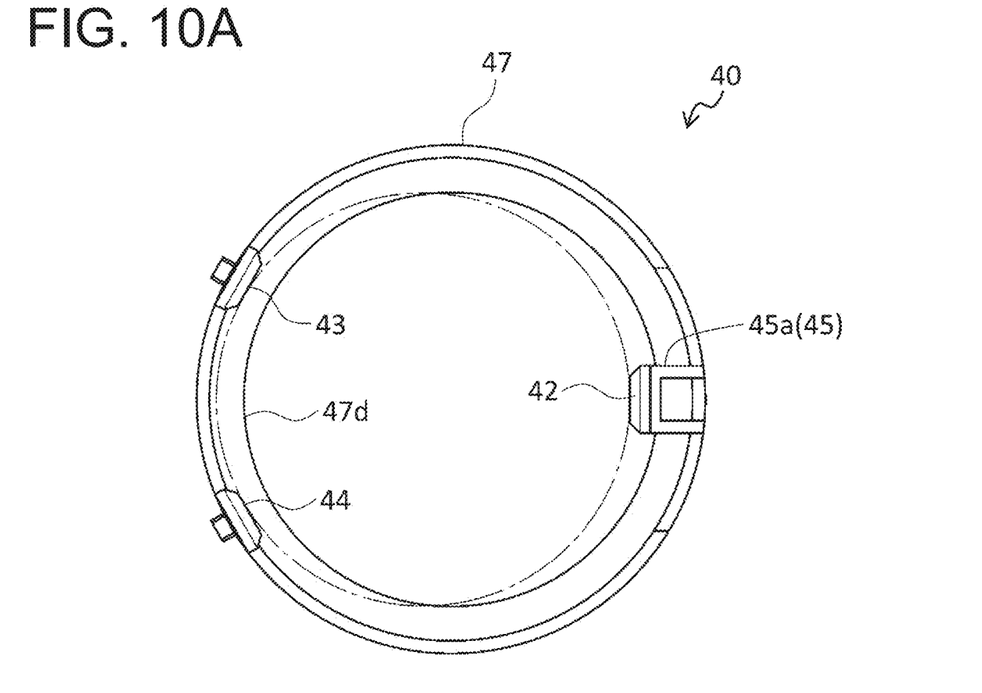
FIG. 10A is a top view of a state before a lens cap unit according to the second embodiment is attached to a housing.
Figure 10B:
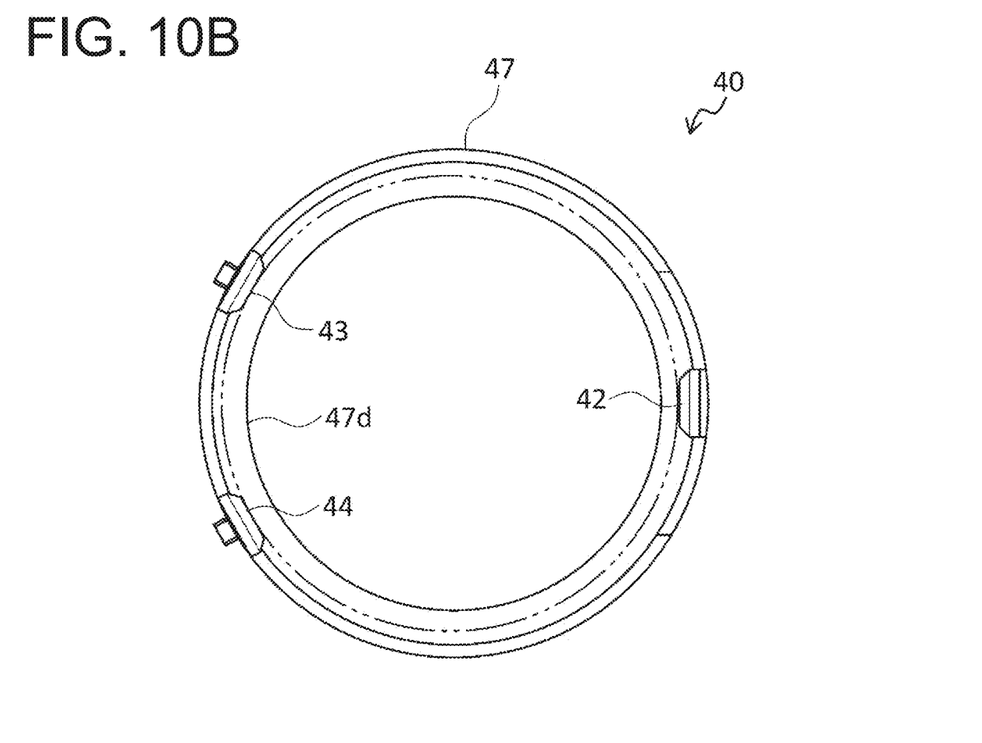
FIG. 10B is a top view of a state before a lens cap unit according to the second embodiment is attached to a housing.

FIG. 6 is an exploded perspective view of a lens cap unit 40 according to the second embodiment as viewed obliquely from above. FIG. 7 is an exploded perspective view of the lens cap unit 40 according to the second embodiment viewed obliquely from below. FIG. 8 is an assembled perspective view of the lens cap unit 40 according to the second embodiment. FIG. 9 is a longitudinal section view of the lens cap unit 40 according to the second embodiment. FIG. 10 is a top view of the lens cap unit 40 according to the second embodiment. In the following, the features which are different from those according to the first embodiment will be mainly described while explanation for the features common therebetween will be omitted. In the first and second embodiments, the components having the common basic functions are provided with the same names.

As illustrated in FIG. 6 to FIG. 10B, the lens cap unit 40 according to the second embodiment mainly includes a cap main body 41, a plurality of protrusions 42, 43, 44 (three in the present embodiment), a spring body 45 (an example of the biasing member), and a protective lens unit 50.

The cap main body 41 is, for example, a member made of resin (for example, polypropylene) and formed with a combination of a base plate 46, a cylindrical body 47, and a housing portion 48. The base plate 46 is a flat plate-shaped portion. To the base plate 46, the outer edge portion of the through hole 21 of the drape main body 20 is welded. The base plate 46 is provided with a through hole 46a penetrating the base plate 46 in the thickness direction. The cylindrical member 47 protrudes from the lower surface of the base plate 46 so as to surround the through hole 46a. The housing portion 48 is formed on the lower surface of the base plate 46 so as to project from the outer curved surface of the cylindrical body 47.

The cylindrical body 47 according to the second embodiment differs from the cylindrical body 37 according to the first embodiment in the following points. Firstly, the end on the other side of the cylindrical body 47 in the axial direction is perpendicular to the axial direction of the cylindrical body 47. Secondly, the cylindrical member 47 is provided with through holes 47a, 47b, 47c, a contact ring 47d (contact portion), a cut-out 47e, and a recessed groove 47f.

The through holes 47a to 47c penetrate the cylindrical body 47 in the thickness direction, at positions spaced apart from each other in the circumferential direction of the cylindrical body 47. The through holes 47a to 47c are provided on the side closer to the base plate 46 than the contact ring 47d in the axial direction of the cylindrical member 47. Into the through holes 47a to 47c, the protrusions 42 to 44, which will be described later, are inserted. That is, the through hole 47a allows the internal space of the cylindrical member 47 to communicate with the internal space of the housing portion 48. The positions of the through holes 47b, 47c are the same as those of the protrusions 32 to 34 described in the first embodiment.

The contact ring 47d protrudes inwardly in the radial direction from the inner curved surface of the cylindrical member 47. The contact ring 47d according to the present embodiment is consecutive in the circumferential direction. However, the contact ring 47d may be provided only on a part of the inner curved surface of the cylindrical member 47. The contact ring 47d is brought into contact with the distal end of the housing 8 inserted into the cylindrical body 47 from above the base plate 46, whereby the amount of insertion of the housing 8 into the cylindrical body 47 is controlled.

The cut-out 47e is provided on the end on the other side of the cylindrical body 47 in the axial direction (on the side opposite to the side where the base plate 46 is positioned), at a portion of the cylindrical body 47 in the circumferential direction (position where the housing portion 48 is provided). In other words, the cut-out 47e is provided on the side opposite to the side on which the base plate 46 is provided, with the contact ring 47d interposed therebetween. The cut-out 47e is a space through which a cover 53 of the protective lens unit 50 passes.

The recessed groove 47f is provided on the inner curved surface of the cylindrical member 47, on the side opposed to the side where the base plate 46 is positioned, with the contact ring 47d interposed therebetween. The recessed groove 47f is consecutive in the circumferential direction of the cylindrical member 47. However, the recessed groove 47f is divided at the position of the cut-out 47e. The recessed groove 47f receives projections 54 provided in a ring portion of the protective lens unit 50, whereby the protective lens unit 50 is fixed to the cap main body 41.

The housing portion 48 is a portion having a frame shape, which defines a space for housing the spring body 45 therein. One end of the housing portion 48 in the axial direction is closed by the base plate 46. On the other hand, the other end of the housing portion 48 in the axial direction is allowed to be opened and closed by the cover 53 of the protective lens unit 50. Inside the housing portion 48, a pin 48a protruding from the lower surface of the base plate 46 is formed.

The basic structures and functions of the protrusions 42 to 44 according to the second embodiment are the same as those of the protrusions 32 to 34 according to the first embodiment. The protrusion 42 is the "movable protrusion 42", and the protrusions 43, 44 are "fixed protrusions 43, 44". As illustrated in FIG. 9A, the protrusion 42 includes a neck portion 42a, a head portion 42b, and a contact portion 42c. In the following, the structure of the protrusion 42, which is common to those of the protrusions 43, 44, will be described in detail.

The neck portion 42a is a portion to pass through a connecting portion 45a of the spring member 45. The head 42b is formed at one end of the neck portion 42a. The head portion 42b is larger than the opening area of the connecting portion 45a. Furthermore, the head 42b is tapered towards its distal end. The contact portion 42c is formed at the other end of the neck portion 42a. The contact portion 42c is larger than the opening area of the connecting portion 45a. Furthermore, the contact portion 42c is a portion that is brought contact with the outer curved surface of the housing 8.

Pressing the head portion 42b into the connecting portion 45a from the side of the inner curved surface of the cylindrical member 47 causes the tapered head portion 42b to be elastically compressed so as to pass through the connecting portion 45a. In this state, as illustrated in FIG. 9A, the neck portion 42a is positioned within the connecting portion 45a, and the contact portion 42c is protruding inside of the cylindrical member 47. In the same manner as above, pressing head portions 43b, 44b into the through holes 47b, 47c from the side of the inner curved surface of the cylindrical member 47 causes the tapered head portions 43b, 44b to be elastically compressed so as to pass through the through holes 47b, 47c. In this state, neck portions 43a, 44a are positioned in the through holes 47b, 47c, head portions 43b, 44b are positioned outside the cylindrical body 47, and contact portions 43c, 44c are positioned inside the cylindrical body 47.

The spring body 45 is a further example of the biasing member for biasing the movable protrusion 42 in the direction of protruding from the inner curved surface of the cylindrical body 47. That is, the biasing member is not limited to the coil spring 35 according to the first embodiment but can employ the ones having various shapes. As illustrated in FIG. 6 and FIG. 7, the spring member 45 is, for example, a member made of resin (for example, polyacetal) and formed with a combination of the connecting portion 45a, a fixing portion 45b, and a pair of flat springs 45c, 45d.

The connecting portion 45a is a portion having the opening to which the head portion 42b of the projection 42 is connected. The fixing portion 45b is a portion for receiving the pin 48a to fix the spring member 45 within the housing portion 48. The flat springs 45c, 45d are elastically compressed with their one ends being connected to the connecting portion 45a and their other ends being connected to the fixing portion 45b. The movable protrusion 42 is attached to the connecting portion 45a and the pin 48a is inserted into the fixed portion 45b, whereby, as illustrated in FIG. 8A and FIG. 10A, the movable protrusion 42 protrudes inwardly in the radial direction from the inner curved surface of the cylindrical member 47.

The protective lens unit 50 is a member for fixing the protective lens 52 to the cap main body 41 with the protective lens 52 being tilted relative to the optical axis L0. As illustrated in FIG. 6 and FIG. 7, the protective lens unit 50 is, for example, a member made of resin (for example, polycarbonate) and formed with a combination of a ring portion 51, the protective lens 52, and the cover 53.

The ring portion 51 is formed to have a substantially cylindrical shape. The ring portion 51 is a portion to be inserted into the cylindrical body 47. That is, the outer diameter dimension of the ring portion 51 is set to be the same as or slightly less than the inner diameter dimension of the cylindrical body 47. On an outer curved surface of the ring portion 51, projections 54 are formed. The projections 54 protrude outwardly in the radial direction from the outer curved surface of the ring portion 51 and extend in the circumferential direction of the ring portion 51, respectively. The ring portion 51 is inserted into the cylindrical body 47 and the projections 54 enter the recessed groove 47f, whereby the protective lens unit 50 is fixed to the cap main body 41. However, the method of fixing the protective lens unit 50 to the cap main body 41 is not limited thereto, and it may be carried out by bonding, welding, fastening using a bolt, or a combination thereof.

The basic structures and functions of the protective lens 52 according to the second embodiment are the same as those of the protective lens 36 according to the first embodiment. The protective lens 52 is positioned inside the ring portion 51. More specifically, in the state where the protective lens unit 50 is fixed to the cap main body 41, the protective lens 52 is arranged within the ring portion 51 so as to be tilted relative to the optical axis L0.

The cover 53 is a portion protruding outwardly in the radial direction, from a portion of the ring portion 51 in the circumferential direction. In the state where the ring portion 51 is inserted into the cylindrical body 47, the cover 53 closes the housing portion 48. This prevents the spring body 45 from falling off.

According to the second embodiment, the same operations and effects as those of the first embodiment can be obtained. Furthermore, according to the second embodiment, pressing the cylindrical member 47 into the housing 8 until the distal end of the housing 8 is contact with the contact ring 47d enables the distance between the objective lens 6 and the protective lens 52 to be set appropriately. As a result, the operation of attaching the microscope drape 10 to the surgical microscope 1 is further facilitated.

REFERENCE SIGNS LIST

1 . . . surgical microscope, 2, 3, 4, 5 . . . arm, 6 . . . objective lens, 7 . . . eyepiece lens, 8 . . . housing, 10 . . . microscope drape, 20 . . . drape main body, 21, 37a, 46a, 47a, 47b, 47c . . . through hole, 30, 40 . . . lens cap unit, 31, 41 . . . cap main body, 32, 33, 34, 42, 43, 44 . . . protrusion, 35 . . . coil spring, 36, 52 . . . protective lens, 37, 47 . . . cylindrical body, 38, 48 . . . housing portion, 45 . . . spring body, 46 . . . base plate, 47d . . . contact ring, 47e . . . cut-out, 47f . . . recessed groove, 48a . . . pin, 50 . . . protective lens unit, 51 . . . ring portion, 53 . . . cover, 54 . . . projection

The invention claimed is:
1. A microscope drape comprising:
a lens cap unit to be attached to and detached from a housing of an objective lens of a surgical microscope;
a protective lens for protecting the objective lens; and
a drape main body for covering the surgical microscope, wherein
the lens cap unit includes:
  a cylindrical body having an inner diameter being larger than that of the housing; and
  a plurality of protrusions provided at positions spaced apart from each other in a circumferential direction of the cylindrical body to protrude inwardly in respective radial directions from an inner curved surface of the cylindrical body;
the plurality of protrusions includes:
  a movable protrusion supported so as to be retractable in the cylindrical body; and
  at least one fixed protrusion fixedly protruding from the inner curved surface of the cylindrical body,
the lens cap unit further includes a biasing member for biasing the movable protrusion in a direction of protruding from the inner curved surface of the cylindrical body, and
the protective lens is supported at a distal end of the cylindrical body with being tilted with respect to an optical axis of the objective lens.
2. The microscope drape according to claim 1, wherein each of the plurality of protrusions is provided at one of three positions spaced apart from each other in the circumferential direction of the cylindrical body, respectively.

3. The microscope drape according to claim 2, wherein
the plurality of protrusions provided at the three positions includes:
- the movable protrusion; and
- two fixed protrusions including the at least one fixed protrusion, and in the circumferential direction of the cylindrical body, a distance between the two fixed protrusions is less than a distance between the movable protrusion and each of the fixed protrusions.

4. The microscope drape according to claim 1, wherein
the lens cap unit includes a cap main body formed with a combination of the cylindrical body and a housing portion extending from an outer curved surface of the cylindrical body to house the biasing member therein, the cylindrical body is provided with a through hole communicating with the housing portion, the lens cap unit further includes a protective lens unit for fixing the protective lens to the cap main body with the protective lens being tilted relative to the optical axis, and the protective lens unit is formed with a combination of a ring portion to be inserted into the cylindrical body, the protective lens positioned inside the ring portion, and a cover for closing the housing portion in a state where the ring portion is inserted into the cylindrical body.

5. The microscope drape according to claim 4, wherein
on the inner curved surface of the cylindrical body, a recessed groove extending in the circumferential direction of the cylindrical body is formed, and on an outer curved surface of the ring portion, a projection extending in a circumferential direction of the ring portion to enter the recessed groove is formed.

6. The microscope drape according to claim 4, wherein
the cap main body is made of polypropylene, and
the protective lens unit is made of polycarbonate.

7. The microscope drape according to claim 1, wherein
the lens cap unit includes a contact portion protruding inwardly in a radial direction from the inner curved surface of the cylindrical body to be in contact with a distal end of the housing.

* * * * *